US012083358B2

(12) United States Patent
Bengtsson et al.

(10) Patent No.: US 12,083,358 B2
(45) Date of Patent: Sep. 10, 2024

(54) METHOD AND SYSTEM FOR ROBUST RADIOTHERAPY TREATMENT PLANNING FOR DOSE MAPPING UNCERTAINTIES

(71) Applicant: RaySearch Laboratories AB (Publ), Stockholm (SE)

(72) Inventors: Ivar Bengtsson, Stockholm (SE); Albin Fredriksson, Stockholm (SE)

(73) Assignee: Raysearch Laboratories AB (publ), Stockholm (SE)

( * ) Notice: Subject to any disclaimer, the term of this patent is extended or adjusted under 35 U.S.C. 154(b) by 1 day.

(21) Appl. No.: 18/186,773

(22) Filed: Mar. 20, 2023

(65) Prior Publication Data
US 2023/0302298 A1 Sep. 28, 2023

(30) Foreign Application Priority Data

Mar. 22, 2022 (EP) ..................................... 22163558

(51) Int. Cl.
*A61N 5/10* (2006.01)
(52) U.S. Cl.
CPC ......... *A61N 5/1039* (2013.01); *A61N 5/1031* (2013.01); *A61N 5/1038* (2013.01)

(58) Field of Classification Search
None
See application file for complete search history.

(56) References Cited

U.S. PATENT DOCUMENTS

| | | | | |
|---|---|---|---|---|
| 2015/0124930 A1* | 5/2015 | Verhaegen | ........... | A61N 5/1047 250/252.1 |
| 2017/0014642 A1 | 1/2017 | An et al. | | |
| 2019/0329072 A1* | 10/2019 | Magro | ..................... | G01T 1/161 |
| 2021/0220671 A1* | 7/2021 | Eriksson | .............. | A61N 5/1037 |
| 2023/0144962 A1* | 5/2023 | Andersson | ............. | A61N 5/103 378/65 |

FOREIGN PATENT DOCUMENTS

| | | |
|---|---|---|
| WO | 2012069965 A1 | 5/2012 |
| WO | 2016070938 A1 | 5/2016 |
| WO | 2021184161 A1 | 9/2021 |

OTHER PUBLICATIONS

Communication under Rule 71(3) EPC dated Jan. 29, 2024, European Patent Office, Munich, Germany.
Extended European Search Report, Aug. 31, 2022, European Patent Office, Munich, Germany.

* cited by examiner

*Primary Examiner* — Hoon K Song
(74) *Attorney, Agent, or Firm* — Noréns Patentbyrå AB (57) ABSTRACT

Generating a robust radiotherapy treatment plan for a treatment volume, defined using a plurality of voxels, of a subject. A first and at least one second image of the treatment volume are received. A distribution of mapped doses in the first image is generated by mapping a dose defined in the at least one second image to the first image using image registration. An optimization problem is defined using at least one optimization function for a total dose, related to the radiotherapy treatment. At least one optimization function value is calculated based on at least two mapped doses in the distribution of mapped doses in the first image. A radiotherapy treatment plan is generated by optimizing the at least one optimization function value evaluated by taking into account the at least two mapped doses in the distribution of mapped doses.

14 Claims, 4 Drawing Sheets

Delivered dose on old image

Mapped dose on new image

First image

Fig. 3a

Second image

Fig. 3b

First image

Fig. 4a

Second image

METHOD AND SYSTEM FOR ROBUST RADIOTHERAPY TREATMENT PLANNING FOR DOSE MAPPING UNCERTAINTIES

TECHNICAL FIELD

The present disclosure relates in general to the field of radiotherapy treatment, in particular, the generation, optimization, and evaluation of a radiotherapy treatment plan.

BACKGROUND ART

Medical imaging is used extensively in radiotherapy treatment planning to identify and delineate targets (tumors) and organs-at-risk (OARs) in the patient. Together with other radiotherapy plan parameters such as minimum or target dose to be delivered to the tumor and maximum dose for the OARs, the delineated targets and OARs from the acquired images serve as input to optimize the planned dose distribution such that radiation is concentrated to the target while limiting exposure of the OARs.

In many treatment situations multiple images of the patient are acquired at different points in time and/or space. Examples include but are not limited to adaptive planning in which the original plan is adapted over the course of the radiotherapy treatment, retreatment in which the patient is undergoes additional radiotherapy treatment, and 4-dimensional robust optimization in which multiple images are acquired, e.g., over a breath cycle.

In order to compare medical images of the same patient acquired at different times and/or from different points of view and obtain information of delivered doses, the images undergo image registration (IR) to transform the different sets of data into one coordinate system, e.g., one first image. However, during the course of radiotherapy treatment, changes may occur which affect the precision in the dose delivery and spatial distribution of the effective dose. Such changes can include tumor shift, shrinkage or expansion, or changes in shape of the tumor and surrounding anatomy in the patient, e.g., due to weight loss/gain.

To mitigate the effects of anatomical changes, deformable image registration (DIR) is used, in which individual volume elements are mapped from one image to another image using non-rigid translations and/or rotations, resulting in a deformation map or deformation vector field (DVF). Nevertheless, since there is no well-behaved deformation that perfectly deforms all anatomical regions, current methods of DIR are ambiguous and therefore any dose mapping based on DIR is inherently uncertain.

The prior art does not accurately take this uncertainty into account. Rather, the choice is between trusting the deformation vector field (DVF) in a region or rejecting it completely, applying a potentially overly conservative estimate as the mapped dose.

WO 2012/069965 A1 discloses a system and method for manually or automatically correcting a deformation map resulting from registration of two planning image sets. However, the correction process is time-consuming, requires user expertise and does not sufficiently overcome the uncertainty in the dose mapping.

SUMMARY OF THE INVENTION

An object of the present disclosure is to provide an improved solution wherein a robust optimization approach is provided to handle dose mapping uncertainties in image registration. This object is achieved in a first aspect of the present disclosure, in which there is provided a method for generating a robust radiotherapy treatment plan for a treatment volume of a subject, said treatment volume being defined using a plurality of voxels, the method comprising the steps of:
receiving a first image of the treatment volume;
receiving at least one second image of the treatment volume;
generating a distribution of mapped doses in the first image by mapping a dose defined in the at least one second image to the first image using image registration;
defining an optimization problem using at least one optimization function for a total dose related to the radiotherapy treatment, wherein the total dose is a function of a dose defined in the first image and the dose defined in the at least one second image;
calculating at least one optimization function value based on at least two mapped doses in the distribution of mapped doses in the first image; and
generating a radiotherapy treatment plan by optimizing the at least one optimization function value evaluated by taking into account the at least two mapped doses in the distribution of mapped doses.

By considering the DVF as uncertain within reasonable limits, or considering multiple plausible DVFs, the present disclosure makes it possible to obtain a total dose which is robust to the modelled dose mapping uncertainty. The main advantage is that by considering a distribution of mapped doses rather than only a nominal mapped dose, it is possible to guide the optimizer to solutions that ensure adequate total dose, even in regions of sharp dose gradients and IR uncertainty.

The present disclosure provides robustness with respect to uncertainties regarding what has already been delivered, while conventional methods only consider what will be delivered in the future. Moreover, the generation of the distribution of mapped doses in the first image can be done in several ways and is not limited to any specific dependency structure between the voxels in the treatment volume. In this context, a distribution can be defined as a set of mapped doses, and optionally, corresponding probabilities for each member in the set. Alternatively, the distribution can be defined as nominal value and an error estimate. These could for example be the mean value per voxel and the standard deviation per voxel, or alternatively the maximal deviation per voxel.

In one embodiment, mapping the dose in the at least one second image to the first image is performed using deformable image registration (DIR). DIR can account for non-rigid translations, rotations and/or other changes in the anatomy.

In one embodiment, mapping the dose in the at least one second image to the first image is performed using at least two different image registrations, wherein the distribution of mapped doses is the set containing the at least two mapped doses. Increasing the number of image registrations, e.g., using several different algorithms or algorithm parameter choices, provides a more reliable estimation of the dose mapping uncertainty.

In one embodiment, mapping the dose in the at least one second image to the first image is performed by making an error estimate for each vector in the deformation vector field resulting from the image registration, wherein the distribution of mapped doses is based on at least two mapped doses resulting from the deformed vector field perturbed according to the error estimate using at least two different perturbations. One of the perturbations can be the zero perturbation.

In one embodiment, the dose in the at least one second image is a dose from a previous treatment, treatment fraction or partial treatment fraction, and wherein the step of generating a radiotherapy treatment plan comprises generating a radiotherapy retreatment plan or adapting a pre-existing radiotherapy treatment plan.

In one embodiment, the dose in the at least one second image is a partial beam dose in a 4-dimensional radiotherapy treatment plan.

In one embodiment, the optimization problem comprises constraints which define parameters that are maintained during the optimization. The constraints may be e.g. in the form of predetermined doses in a defined sub-volume (e.g. the target), which are not changed during optimization. In this way, the target dose is maintained to ensure a certain dose distribution, but the remaining portions of the radiotherapy treatment plan are robustly optimized.

In one embodiment, the optimization problem comprises a biological or a physical goal. Preferably, the physical goal comprises dose limits to targets and organs at risk (OAR) in the treatment volume, dose volume histogram (DVH) limits, LET limits, the location where the particles stop and/or homogeneity and conformity indices. In this way, biological uncertainties can also be combined with other (physical) objectives. Plan optimization and evaluation should be able to use different biological models in combination as well as in combination with physical optimization functions and goals. The optimization problem could be a combination of physical goals such as minimum and maximum doses to targets and organs at risk, respectively, and DVH limits, and biological goals such as BED, EQD2, EUD, TCP, and NTCP.

In one embodiment, the physical goal comprises dose limits to targets and organs at risk (OAR) in the treatment volume, dose volume histogram (DVH) limits, linear energy transfer (LET) limits, the location where the particles stop and/or homogeneity and conformity indices.

In one embodiment, the optimization comprises a stochastic programming approach, wherein the expected value of the optimization function over the at least two mapped doses in the distribution of mapped doses is minimized; a minimax approach, wherein the maximum of the optimization function over the at least two mapped doses in the distribution of mapped doses is minimized; or any combination of the two commonly referred to as minimax stochastic programming; or a voxel-wise worst-case approach, in which the worst-case dose to each voxel considered individually is optimized.

In one embodiment, the at least two mapped doses in the distribution of mapped doses are further combined with an additional set of error scenarios, wherein the additional set of error scenarios represents specific realizations of the uncertainty of one or more parameters relevant for treatment planning, comprising particle range, spatial position of the treatment volume, radiotherapy treatment apparatus setup, density of irradiated tissue, interplay effects, organ movement and/or biological model parameter values.

According to a second aspect, there is provided a computer program product comprising computer-readable code means which, when run in a computer, will cause the computer to perform the method according to the first aspect.

According to a third aspect, there is provided a computer system comprising a processor coupled to a memory having stored thereon computer-readable instructions that, when executed by the processor, cause the processor to perform the method according to the first aspect.

According to a fourth aspect, there is provided a treatment planning system comprising a computer system as described above.

BRIEF DESCRIPTION OF DRAWINGS

These and other features, aspects, and advantages of the disclosure will be further explained in the following description with reference to the accompanying drawings, in which.

Herein, identical reference numerals are used, where possible, to designate identical elements that are common to the figures. Also, the images in the drawings are simplified for illustrative purposes and are not necessarily depicted to scale.

DESCRIPTION OF EMBODIMENTS

Figure 1:
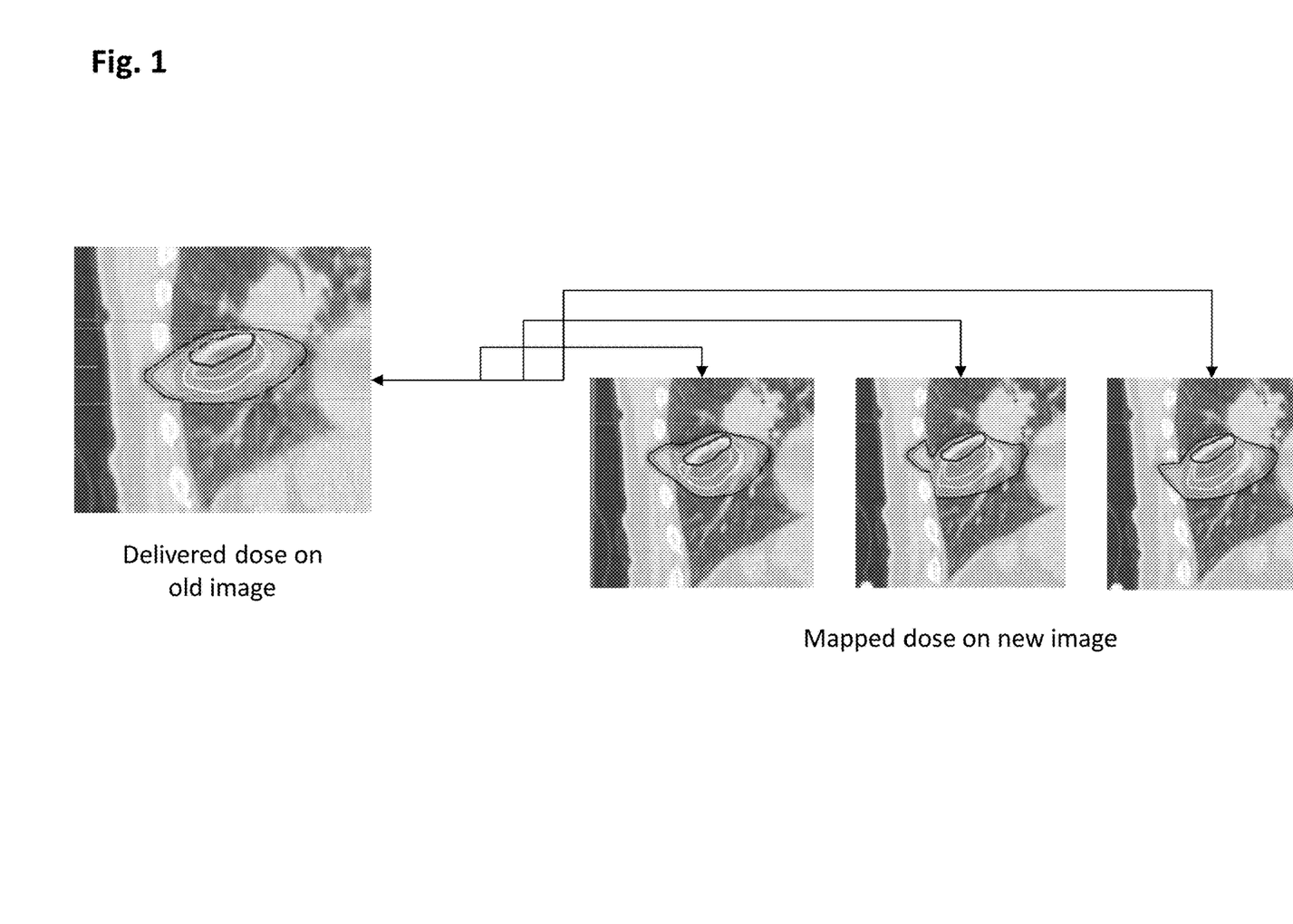
FIG. 1 shows three mappings of a delivered dose on an old image to a new image

Referring now to FIG. 1 the underlying problem of dose mapping uncertainty is illustrated. On the left-hand side of FIG. 1, there is shown an image of a patient wherein a delivered dose is indicated. The different colors of shading indicate the amount of dose delivered to a particular area of a treatment volume. On the right-hand side of FIG. 1, there are shown three different images of the same treatment volume, but at a different point in time. In order to be able to compare or integrate the data obtained from these different images, e.g., to map the delivered dose on the old image to the new image, the old image is registered with the new image by means of image registration. Each of the three images represent different image registrations using different algorithms and yielding three different mapped doses on the new image. Thus, there is an inherent uncertainty in the dose mapping which affects the radiotherapy treatment planning.

Figure 2:
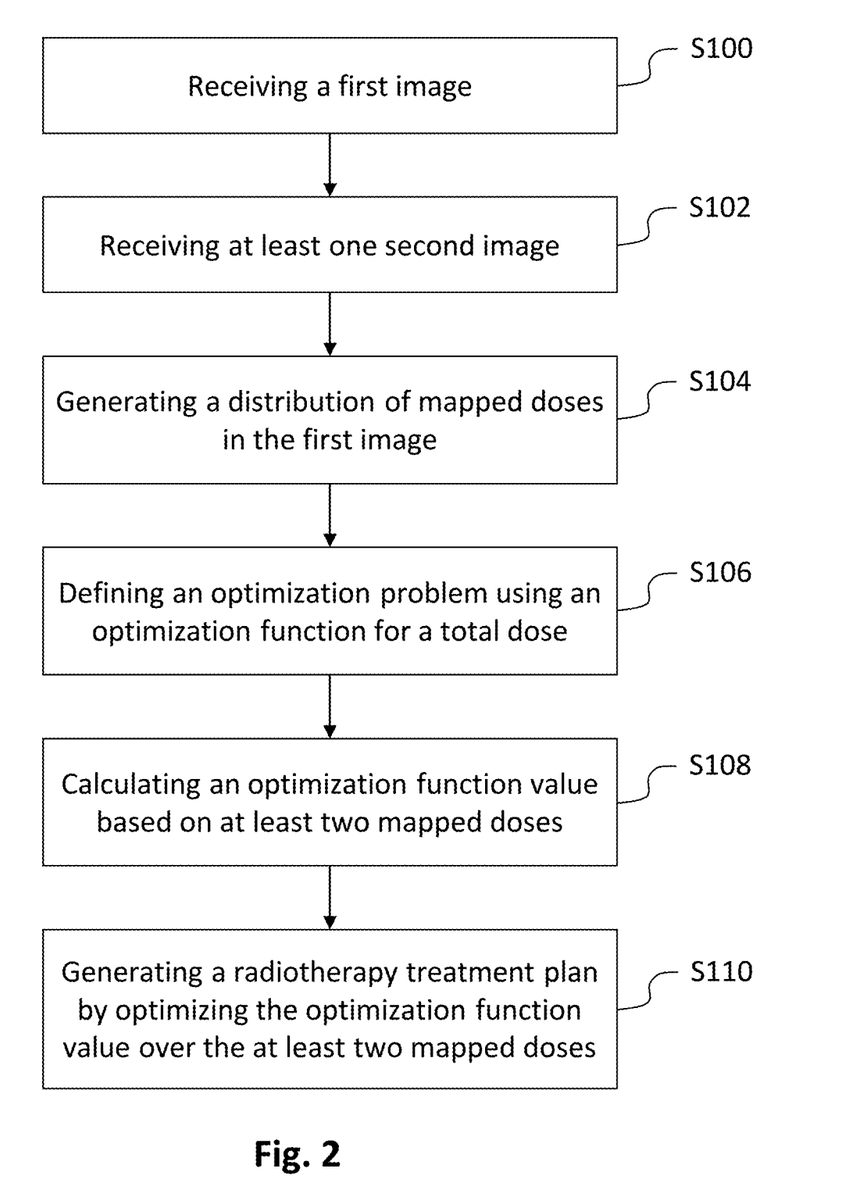
FIG. 2 shows a flow chart representing the steps of a computer-based method for generating a robust radiotherapy treatment plan according to one embodiment of the present disclosure.

FIG. 2 is a flow chart of an embodiment of the method according to the present disclosure, which may be used in conjunction with generating a radiotherapy treatment plan. In one embodiment the starting point is an initial treatment plan and a number of scenarios to consider, and the method aims to obtain an improved treatment plan based on the initial treatment plan, to modify an initial plan with some constraints, or to obtain a deliverable treatment plan in cases where the initial treatment plan does not satisfy all machine limitations. Depending on the type of data included in the plan, other input data may be needed, for example, data related to the patient, for dose calculation. The initial treatment plan may be obtained in any manner known in the art, including scenario-based and non-scenario-based methods.

The treatment plan is generated with the purpose of providing radiotherapy treatment of a treatment volume of a subject (patient) which may be an organ and includes a target which may be a tumor or cluster of tumor cells. The treatment volume is defined using a plurality of voxels, as known in the art.

In step S100, a first image of the treatment volume is received. The first image may be a reference image representative of a current state of the patient to be used in radiotherapy treatment planning. In step S102, at least one second image of the treatment volume is received. The second image may be a target image representative of a state of the patient at a previous point in time, e.g., during a previous treatment or treatment fraction. Alternatively, the second image may be a phase image representative of a state of the patient in a different phase, e.g., at a different phase of the breathing cycle of the patient.

Both the first and second images may be obtained using any suitable technique of medical imaging including, but not limited to X-ray computed tomography (CT), magnetic resonance imaging (MRI), positron emission tomography (PET), ultrasound and single-photon emission computed tomography (SPECT).

In step S104, a dose defined in the at least one second image is mapped to the first image using image registration, thus generating a distribution of mapped doses in the first image. In one embodiment, deformable image registration is used, taking into account non-rigid translations, rotations and/or other changes to the anatomy. The image registration yields a deformation vector field in which a vector representing the deformation between the first image and the second image is assigned to each voxel in the treatment volume.

In step S106, an optimization problem is defined using at least one optimization function for a total dose related to the radiotherapy treatment. The total dose is a function of a dose defined in the first image and the dose defined in the at least one second image In step S108, an optimization function value is calculated based on at least two mapped doses in the distribution of mapped doses in the first image. The optimization function value calculation could be performed by using the mapped dose and the dose defined in the first image as input variables, yielding one optimization function value. Alternatively, each of the mapped doses could be used as input variables, wherein the first function value is based on a first mapped dose and the second function value is based on a second mapped dose.

In step S110, the optimization function value is optimized, evaluated by taking into account the at least two mapped doses in the distribution of mapped doses to generate a radiotherapy treatment plan.

Figure 3A:
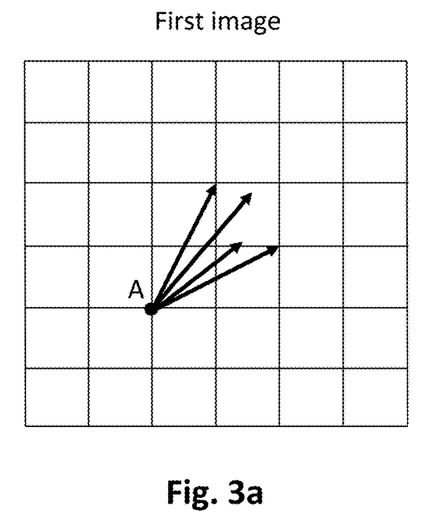
FIGS. 3a and 3b illustrate generation of a distribution of mapped doses according to one embodiment of the present disclosure.
Figure 3B:
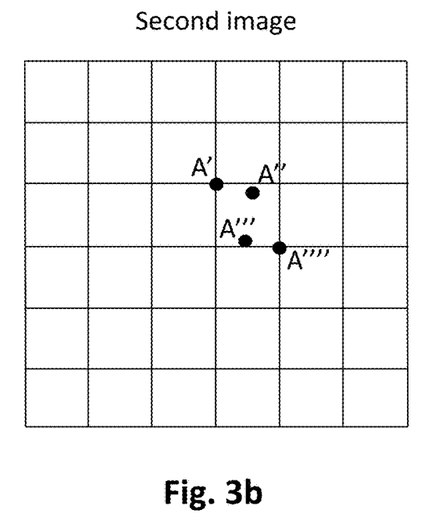

The distribution of mapped doses may be generated in several ways and is not limited to any specific dependency structure between the voxels. Referring now to FIGS. 3a and 3b there is shown an illustration of one embodiment, in which at least two different image registrations are used to map the dose in the at least one second image to the first image. FIG. 3a shows a first image including a point A, and four arrows representing the mapping of four points A', A'', A''' and A'''' in a second image shown in FIG. 3b to the point A in the first image. Each of the four arrows is then a vector in corresponding deformation vector fields resulting from four different image registrations.

The set of the mapped doses may be considered as the distribution of mapped doses. By increasing the number of image registrations, i.e., using several different image registration algorithms, or using the same algorithm with different settings or with different perturbations added, a more reliable estimation of the dose mapping uncertainty is achieved.

Figure 4A:
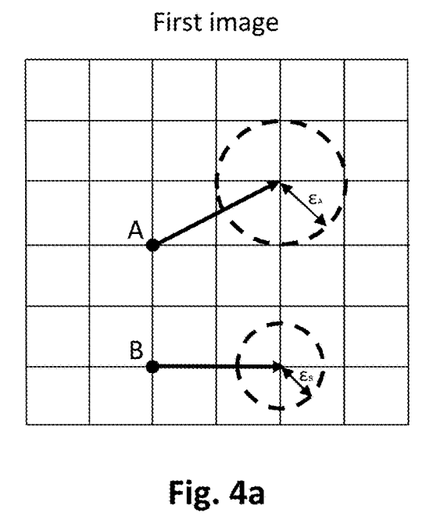
FIGS. 4a and 4b illustrate generation of a distribution of mapped doses according to another embodiment of the present disclosure.
Figure 4B:
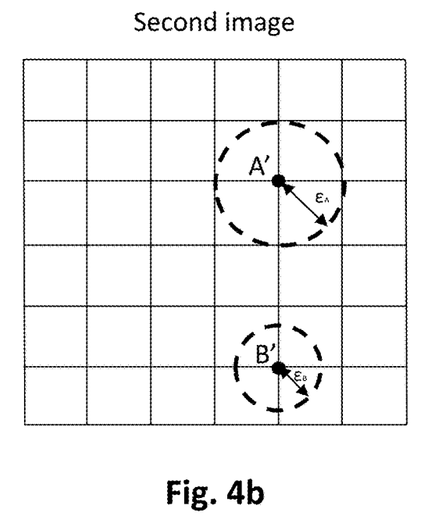

Referring now to FIGS. 4a and 4b, there is shown another embodiment of how to generate the distribution of mapped doses, in which each vector in the deformation vector field is considered as erroneous. FIG. 4a shows a first image including two points A and B, and a vector assigned to each point, respectively, representing the mapping of points A' and B' in a second image shown in FIG. 4b to the points A and B in the first image. The estimate of the error for the two vectors in FIG. 4a is here represented by a circle around point A' and B', respectively, having a radius EA and CB, respectively. This error estimation is then used to generate multiple plausible realizations for each vector to generate the distribution of mapped doses. More specifically, the distribution of mapped doses can be based on at least two mapped doses resulting from the deformed vector field perturbed according to the error estimate, using at least two different perturbations. One of the perturbations can be the zero perturbation, i.e., in which the deformation vector field obtained from the image registration is considered without perturbing the vectors.

The method according to the present disclosure may be used in different planning situations. In one embodiment, the method is used to generate a radiotherapy retreatment plan or adapt a pre-existing radiotherapy treatment plan. In such a case, the dose defined in the at least one second image is a dose from a previous treatment, treatment fraction or partial treatment fraction, herein also called a background dose. The total dose is then the sum of the background dose and the new dose to be delivered in the retreatment plan or adapted plan.

In one embodiment, the method is used to generate a 4-dimensional radiotherapy treatment plan, in which the treatment volume undergoes cyclic spatial deformation during different phases, e.g., of a breathing cycle of the patient. In such a case, the dose defined in the at least one second image is a partial beam dose delivered during a particular phase. The total dose is then the sum of the partial beam doses to be delivered in the 4-dimensional radiotherapy treatment plan.

The optimization function may be included as a constraint in the optimization. Alternatively, the optimization function may be included as an objective function constituent in the optimization. Typically, goals are set for the treatment, and these goals are used to define objective function constituents, constraints or a combination of these. An objective function constituent is a desired goal, towards which the optimization should strive or which the optimization should try to fulfill as well as possible, whereas a constraint is a strict goal or condition that must be satisfied precisely, such as a minimum dose to a tumor or a maximum dose to an OAR or bounds on the variables controlling the objective function.

Various types of optimization methods for achieving robustness can be used in conjunction with the method according to the present disclosure. For example, minimax (or "composite worst-case") optimization can be used, in which the worst-case scenario over the composite objective function is optimized. The optimization problem is then formulated as $$\min_{x \in X} \max_{s \in s} f(x; s),$$

wherein X is the set of feasible optimization variables (e.g., the set of allowed spot weights, MLC leaf positions, etc.), S is the set of scenarios enumerating the different mapped doses, and $$f(x;s)$$

is the composite objective as a function of the optimization variables x under scenario s. For example, f(x;s) could be given by g(d(x)+$d_b$(s)), where d(x) is the new dose resulting from the optimization variables x, $d_b$(s) is the background dose (i.e., the mapped dose) under scenario s, and g is a function relating to the total dose d(x)+$d_b$(s).

Another type of optimization method to achieve robustness is expected value optimization, in which the expected value over the uncertainties is optimized. The optimization problem is formulated as $$\min_{x \in X} Ef(x;Y),$$

wherein E is the expectancy operator and Y is a random variable taking on values from the set S of scenarios.

A third alternative is the voxel-wise worst-case optimization method. In this method, two artificial worst-case dose distributions, $d^{high}$ and $d^{low}$ are calculated based on the mapped doses. Here, $d^{high}$ is calculated as the highest mapped dose over the scenarios to each voxel considered individually, and $d^{low}$ is calculated as the lowest mapped dose over the scenarios to each voxel considered individually, i.e., $$d_i^{high} = \max_{s \in S} d_{b,i}(s), i = 1, \ldots, N$$

$$d_i^{low} = \min_{s \in S} d_{b,i}(s), i = 1, \ldots, N$$

where $d_{b,i}$(s) denotes the mapped dose to voxel i under scenario s and N is the number of voxels.

The optimization problem is then formulated as $$\min_{x \in X} f^{high}(d(x) + d^{high}) + f^{low}(d(x) + d^{low}),$$

where $f^{high}$ is a composite objective function with constituents that are used to avoid overdosage (e.g., objectives for the organs at risk, OAR) and $f^{low}$ is a composite objective function with constituents that are used to avoid underdosage (e.g., minimum dose requirements for the target).

Another alternative is to minimize an objective function h(x) not necessarily (but possibly) relating to the full set S of scenarios, and to include constraints for functions f(x; s) for all s in S, i.e., $$\min_{x \in X} h(x)$$

subject to $f(x;s) \leq 0, s \in S.$

The objective function h(x) can be formulated in accordance with any of the above methods but can also be formulated to take only the nominal scenario, corresponding to no error, into account.

Other methods, such as the stochastic minimax method, which is a combination of composite worst-case optimization and expected value optimization, can also be used and are known in the art.

Figure 5:
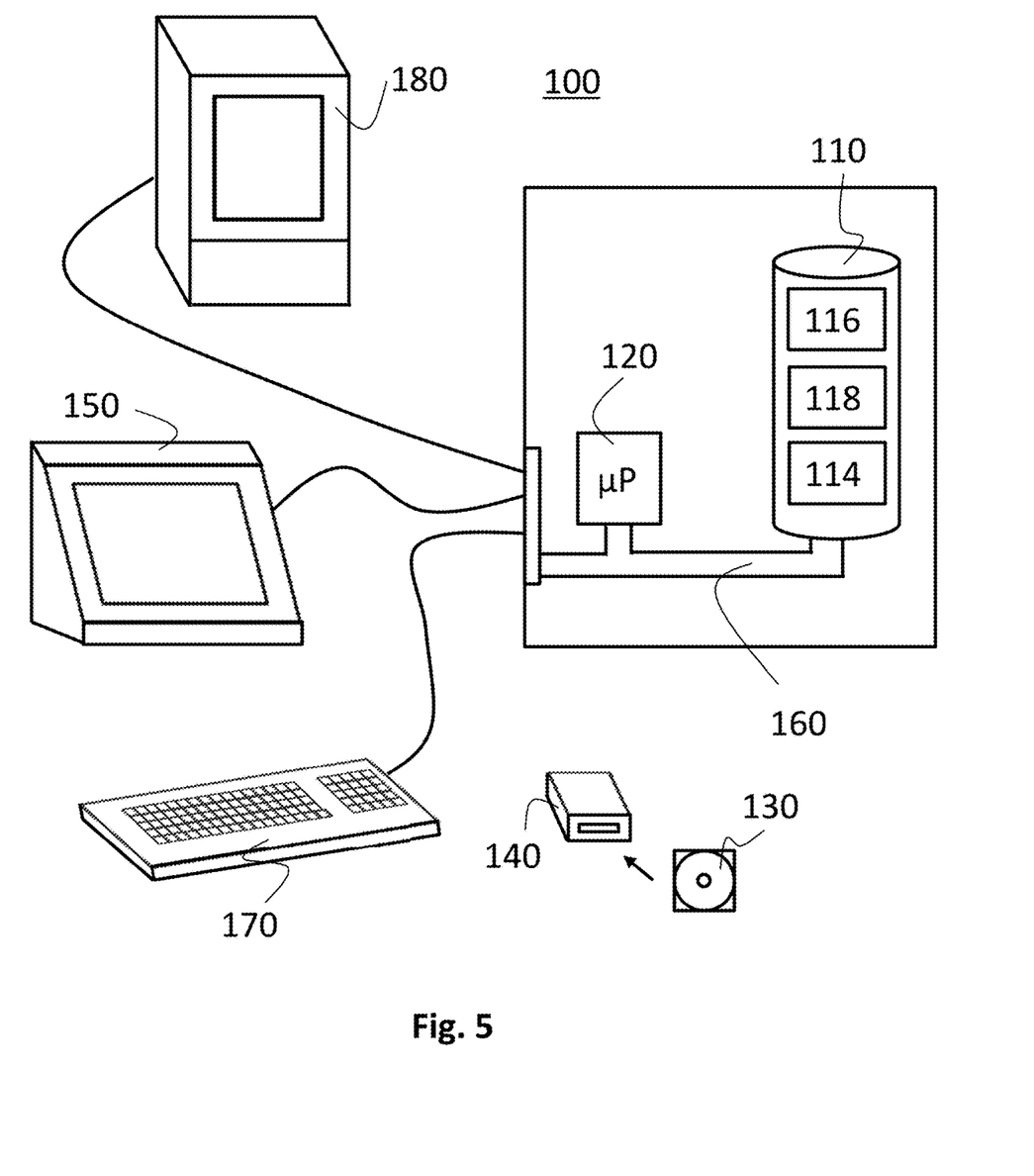
FIG. 5 schematically shows a computer-based system for evaluating, visualizing, generating and improving a radiotherapy treatment plan according to one embodiment of the present disclosure.

Referring now to FIG. 5, it shows a simplified schematic representation of a computer-based system 100 for generating a radiotherapy treatment plan 114, according to the disclosure. The computer-based system 100 includes a memory or database 110 having a radiotherapy treatment plan 114 stored thereon, and a computer program 116 for generating an improved radiotherapy treatment plan 118. Memory 110 can be any volatile or non-volatile memory device such as a flash drive, hard drive, optical drive, dynamic random-access memory (DRAM), static random-access memory (SRAM), and any other suitable device for storing information and later information retrieval and use for data processing. Also, the system 100 includes one or more hardware processors 120 for performing data processing, which are able to access the memory 110. The hardware processor 120 can be made of one or more of a central processing unit (CPU), digital signal processor (DSP), reduced instruction set computer (RISC), application specific integrated circuit (ASIC), complex programmable logic device (CPLD), field-programmable gate arrays (FPGA), parallel processor systems, or a combination of these different hardware processor types.

The computer program 116 is made of computer-readable instructions that can be transferred to hardware processor 120 and can be executed by hardware processor 120. When executed on the hardware processor 120, the computer readable instructions will perform a method for generating an improved radiotherapy treatment plan 118. Results of the processing that is performed by the hardware processor 120 when executing the computer program 116 can be stored in memory 110, for example, the improved radiotherapy treatment plan 118, and associated data. Hardware processor 120 can also access the memory 110 via direct memory access (DMA) and can also use a cache memory for storing temporary processing results. The computer program 116 can also be stored on a non-transitory computer-readable medium 130, for example a universal serial bus (USB) flash drive, optical data carriers such as CD-ROM, DVD-ROM, and Blu-Ray disk, floppy disk, swappable hardware drives, USB external hard drive (HDD), or any other portable information storage device, so that the computer program 116 can be transferred to different computing systems, and also be loaded to the memory 110 of system 100. This can be done by connecting the computer readable medium 130 via a data reader/writer 140 to the system 100, for example, an optical drive, USB interface, etc.

Moreover, the system 100 also includes a display unit 150 that has a display driver that allows visualization of results of the data processing, for example to visualize three-dimensional (3D) representations of a target volume of a patient containing, for example, a tumor or cancer cell, and healthy organs-at-risk for which dose delivery has to be prevented, 3D contour data, or two-dimensional (2D) slice representations for various intersection directions and for LET distribution in both the target volume and for organs-at-risk, biological effect (e.g. probability of injury/cell death/side effects), etc. For example, a 3D computer reproduction of a CT scan can be displayed. Also, the display unit 150 can display dose volume histogram (DVH) that summarize 3D dose distribution by using a graphical 2D format. For example, the display unit 150 is configured to show comparative DVH diagrams for volumes of the patient showing a dose contribution of the radiotherapy treatment plan 114, and for the same volumes of the optimized or improved radiotherapy treatment plan 118, so that also the LET distribution can be visually compared.

The display unit 150 is used for displaying a 3D scan of the patient that is made prior to the treatment, during the treatment or after the treatment. For example, a 3D computer reproduction of a CT scan can be displayed. Also, the display unit 150 can display LET, dose and/or DVH that summarizes 3D dose distribution by using a graphical 2D format or using a numerical format. For example, the display unit 150 is configured to show comparative LET diagrams for volumes of the patient showing a cancer cell destruction or dose contribution of the radiotherapy treatment plan 114. This is shown and compared for the same volumes of the optimized or improved radiotherapy treatment plan so that the improvement can be visually compared. Also, it is possible that the display unit 150 is equipped with a touch screen functionality and can display a graphical user interface to operate system 100.

In addition, computer system 100 has a system bus 160 that connects the hardware processor 120, memory 110, the data reader 140, touch screen, and various other data input-output interfaces and peripheral devices that are not shown. For example, the computer system 100 can be connected to a keyboard 170 for data input by a user and may be connected to an external radiotherapy treatment planning device 180 that has created the radiotherapy treatment plan, for example, a powerful special-purpose computer. Also, the system 100 may be connected to a CT scanner that is not shown. For example, external device 180 that created the radiotherapy treatment plan 114 may be able to develop a dose and LET distribution calculation algorithm that is coded into software, has access to radiation data on prescribed dose distribution, and machine calibration data, and patient-specific information on the target volume of and organs-at-risk of the patient. This external device 180 can then deliver the radiotherapy treatment plan 114 to computer system 100 for evaluation, visualization, creating a new plan, improving an existing plan taking the LET distribution into account. However, it is also possible that computer program 116 is run on the external device itself, thereby not only generating the radiotherapy treatment plan 114 but also generating the improved radiotherapy treatment plan 118.

Furthermore, a computer program product is introduced for performing parameter optimization. The computer program product 130 comprises computer-readable code means, which when run in the computer carries out the method described above.

Example 1: Retreatment Planning with Robustness to Background Dose Uncertainty

Certain patients that have undergone radiotherapy may experience a tumor recurrence in the vicinity of a previously treated volume. In these cases, a second course of radiotherapy may be considered, referred to as retreatment or reirradiation. Then, a first image in the form of a planning image on which to plan the retreatment is acquired. A second image in the form of the old planning image of the previous treatment is also considered. To spare healthy tissue from exceeding a certain total fraction corrected dose, retreatment planning must account for the already delivered dose which is present in the second image. The delivered dose can be mapped from the second image to the first image following an image registration, to be used as background dose. However, the image registration and thus also the background dose may be uncertain or ambiguous. Different image registrations may result in different background doses.

Problem: Which mapped dose can be trusted to be used as background dose for retreatment planning based on the total dose?

Suggested solution: Generate a distribution of at least two background doses and optimize the total dose to OARs robustly to account for dose mapping uncertainties.

Define a new treatment plan on a received first image.
Define at least one objective for a total dose on at least one OAR which one would like to optimize robustly against the uncertainty in dose mapping. Examples of such objectives are:
Maximum total physical dose to an OAR
Maximum total biologically equivalent dose (BED), such as EQD2, to an OAR
Define at least one objective for the retreatment dose to the target.
Optionally, define additional error scenarios which represent specific realizations of one or more additional relevant parameters for radiotherapy treatment planning, such as setup errors or range errors.
Receive a second image, from the original treatment plan, and perform image registration between the first and second image to map the delivered dose in the second image to the first.
Generate a distribution of mapped doses and define scenarios based on the distribution of mapped doses, for example in one of the two following ways:
Perform at least one additional image registration with an alternative algorithm or using alternative algorithm parameters. Define a scenario for each resulting mapped dose.
Calculate an error estimate for the image registration and use this to characterize the distribution of mapped doses. Define scenarios based on artificial worst-case dose distributions, for example the stochastic minimax method as described above.
Optimize the retreatment plan using the preferred robust optimization framework.

Example 2: Adaptive Treatment Planning with Robustness to Background Dose Uncertainty During a radiotherapy treatment course, it may be desirable to adapt the original treatment plan to account for changes in the patient's anatomy or previous errors in the treatment delivery. In this case, a first image in the form of a replanning image is acquired. At least one second image in the form of the fraction images of the delivered fractions is also considered. The delivered dose can be mapped from the at least one second image to the first image following an image registration, to be used as background dose. However, the image registration and thus also the background dose may be uncertain or ambiguous. Different image registration techniques may result in different background doses.

Problem: Which mapped dose can be trusted to be used as background dose for adaptive treatment planning based on the total dose?

Suggested solution: Generate a distribution of at least two background doses and optimize the total dose to OARs robustly to account for dose mapping uncertainties.

Define a new adapted treatment plan on a received first image.

Define at least one objective for a total dose which one would like to optimize robustly against the uncertainty in dose mapping. Examples of such objectives could be:
  Maximum total physical dose to an OAR
  Maximum total BED to an OAR
  Minimum total physical dose to a target volume
Optionally, define additional error scenarios which represent specific realizations of one or more additional relevant parameters for radiotherapy treatment planning, such as setup errors or range errors.
Receive at least one second image, from the previously delivered fractions, and perform image registration between the first and the at least one second image to map the delivered dose in the at least one second image to the first.
For each second image, generate a distribution of mapped doses in the first image, for example in one of the two following ways:
  Perform at least one additional image registration with an alternative algorithm or using alternative algorithm parameters.
  Calculate an error estimate for the image registration and use this to characterize the distribution of mapped doses.
Define scenarios based on realizations of the uncertainty in each of the distributions of mapped doses from the at least one second image.
Optimize the retreatment plan using the preferred robust optimization framework.

Example 3: 4D Treatment Planning with Robustness to Dose Mapping Uncertainty When treating tumors in parts of the body which are subject to periodic motion, it may be desirable to be robust to which phase in the motion cycle during which the dose is delivered. For this purpose, multiple images from various phases of the motion cycle are sometimes acquired. The dose to be optimized is then a function of the doses in each of the phase images mapped by DIR to a common reference image.

Problem: Which dose mapping can be trusted to be used as phase dose in a 4D optimized treatment plan?

Suggested solution: Generate at least two mapped doses from at least one phase image to the reference image and optimize the mapped doses robustly to the dose mapping uncertainty.
  Define a 4D treatment plan in a patient volume subject to motion.
  Define at least one objective for a dose in a reference phase image which one would like to optimize robustly against the uncertainty in dose mapping. Examples of such objectives are:
    Maximum total physical dose to an OAR
    Minimum total physical dose to a target volume
  Optionally, define additional error scenarios which represent specific realizations of one or more additional relevant parameters for radiotherapy treatment planning, such as setup errors or range errors.
  Receive at least one second image which is a phase image from a different phase in the motion cycle and perform an image registration between the first and the at least one second image to be used to map the dose in the at least one second image to the first.
  For each second image, generate a distribution of mapped doses in the first image. In this case, the mapped doses will be functions of the optimization variables and change in each iteration of the optimization. The distribution of mapped doses can for example be generated in one of the following ways:
    Perform at least one additional image registration with an alternative algorithm or using alternative algorithm parameters.
    Calculate an error estimate for the image registration and use this to characterize the distribution of mapped doses.
  Define scenarios based on realizations of the uncertainty in each of the distributions of mapped doses from the at least one second image.
  Optimize the retreatment plan using the preferred robust optimization framework.

Preferred embodiments of a method and system for generating a radiotherapy treatment plan have been disclosed above. However, a person skilled in the art realizes that this can be varied within the scope of the appended claims without departing from the inventive idea.

All the described alternative embodiments above or parts of an embodiment can be freely combined or employed separately from each other without departing from the inventive idea as long as the combination is not contradictory.

The following abbreviations are used:
BED biological equivalent dose
CT computer tomography
CTV clinical tumor/target volume
DICOM digital imaging and communications in medicine
DVH dose volume histogram
EHR electronic health record system
EQD equivalent standard fraction dose
EQD2 equivalent dose in 2 Gy fractions
EUD equivalent uniform distribution
eMIX electronic medical information exchange system
GUI graphical user interface
GTV gross tumor/target volume
HIS hospital information system
HIM health information management system
IGRT image-guided radiotherapy
IMRT intensity-modulated radiotherapy
LET linear energy transfer
MLC multileaf collimator
MRI magnetic resonance imaging system
MU monitor units
NTCP normal tissue complication probability
OAR organ at risk
PBS pencil beam scanning
PET positron emission tomography
PTV planning tumor/target volume
QA quality assurance
QC quality control
US ultrasonography
RBE relative biological effectiveness
ROI region of interest
RVS record and verify system
SPECT single photon positron emission tomography
TCP tumor control probability

The invention claimed is:

1. A method for generating a robust radiotherapy treatment plan for a treatment volume of a subject, the treatment volume being defined using a plurality of voxels, the method comprising the steps of:
receiving (S100) a first image of the treatment volume;
receiving (S102) at least one second image of the treatment volume;

generating (S104) a distribution of mapped doses in the first image by mapping a dose defined in the at least one second image to the first image using image registration;

defining (S106) an optimization problem using at least one optimization function for a total dose related to the radiotherapy treatment, wherein the total dose is a function of a dose defined in the first image and the dose defined in the at least one second image;

calculating (S108) at least one optimization function value based on at least two mapped doses in the distribution of mapped doses in the first image; and generating (S110) a radiotherapy treatment plan by optimizing the at least one optimization function value evaluated by taking into account the at least two mapped doses in the distribution of mapped doses.

2. The method according to claim 1, wherein mapping the dose in the at least one second image to the first image is performed using deformable image registration.

3. The method according to claim 1, wherein mapping the dose in the at least one second image to the first image is performed using at least two different image registrations, wherein the distribution of mapped doses is the variation between the at least two mapped doses.

4. The method according to claim 1, wherein mapping the dose in the at least one second image to the first image is performed by making an error estimate for each vector in the deformation vector field resulting from the image registration, wherein the distribution of mapped doses is based on at least two mapped doses resulting from the deformed vector field perturbed according to the error estimate using at least two different perturbations.

5. The method according to claim 1, wherein the dose in the at least one second image is a dose from a previous treatment, treatment fraction or partial treatment fraction, and wherein the step of generating a radiotherapy treatment plan comprises generating a radiotherapy retreatment plan or adapting a pre-existing radiotherapy treatment plan.

6. The method according to claim 1, wherein the dose in the at least one second image is a partial beam dose in a 4-dimensional radiotherapy treatment plan.

7. The method according to claim 1, wherein the optimization problem comprises constraints which define parameters that are maintained during the optimization.

8. The method according to claim 1, wherein the optimization problem comprises a biological or a physical goal.

9. The method according to claim 8, wherein the physical goal comprises dose limits to targets and organs at risk (OAR) in the treatment volume, dose volume histogram (DVH) limits, linear energy transfer (LET) limits, the location where the particles stop and/or homogeneity and conformity indices.

10. The method according to claim 1, wherein the optimization comprises a stochastic programming approach, wherein the expected value of the optimization function over the at least two mapped doses in the distribution of mapped doses is minimized; a minimax approach, wherein the maximum of the optimization function over the at least two mapped doses in the distribution of mapped doses is minimized; or any combination of the two commonly referred to as minimax stochastic programming; or a voxel-wise worst-case approach, in which the worst case dose to each voxel considered individually is optimized.

11. The method according to claim 1, wherein the at least two mapped doses in the distribution of mapped doses are further combined with an additional error scenario, wherein the additional error scenario represents a specific realization of the uncertainty of one or more parameters relevant for treatment planning, comprising particle range, spatial position of the treatment volume, radiotherapy treatment apparatus setup, density of irradiated tissue, interplay effects, organ movement and/or biological model parameter values.

12. A computer program product (130) comprising a non-transitory computer readable medium containing computer-readable instructions which, when executed on a computer, causes the computer to perform the method according to claim 1.

13. A computer system (100) comprising a processor (120) coupled to a memory (110) having stored thereon computer-readable instructions that, when executed by the processor, cause the processor to perform the method according to claim 1.

14. A radiotherapy treatment planning system comprising a computer system (100) according to claim 13.

* * * * *